United States Patent [19]
Mayer et al.

[11] Patent Number: 5,837,888
[45] Date of Patent: Nov. 17, 1998

[54] PROCESS FOR MEASURING VAPOR TRANSMISSION THROUGH MATERIALS

[75] Inventors: William N. Mayer, White Bear Lake; Stephen D. Tuomela, Oakdale; Guss L. Krake, Richfield, all of Minn.

[73] Assignee: Modern Controls, Inc., Minneapolis, Minn.

[21] Appl. No.: 856,441

[22] Filed: May 14, 1997

[51] Int. Cl.$^6$ .................................................. G01N 15/08
[52] U.S. Cl. ................................................................ 73/38
[58] Field of Search .................................. 73/37, 38, 159

[56] References Cited

U.S. PATENT DOCUMENTS

| | | | |
|---|---|---|---|
| 3,286,509 | 11/1966 | Guckman et al. | 73/38 |
| 5,138,870 | 8/1992 | Lyssy | 73/38 |

OTHER PUBLICATIONS

Modern Controls, Inc. Technical Bulletin #007—A dated May 12, 1983, "Testing with High RH on the Ox–Tran Systems".

ASTM Journal of Testing and Evaluation, vol. 12, No. 3, dated May 1984, Article "The Sandwich Method—A Proposed Approach to the Measurement of Oxygen Transmission Rate Through Moisture–Sensitive Barrier Films," Rex C. Wood.

*Primary Examiner*—Michael Brock
*Attorney, Agent, or Firm*—Palmatier, Sjoquist, Voigt & Christensen, P.A.

[57] ABSTRACT

A process for measuring the vapor transmission rate characteristics of a test material by first measuring the vapor transmission through a test chamber and sample material and subsequently repeating the measurement with the test material adjacent the sample material. By subtracting the first measured transmission rate reciprocal from the second measured transmission rate reciprocal, a value is determined which is the reciprocal of the vapor transmission rate characteristic of the test material.

7 Claims, 2 Drawing Sheets

PROCESS FOR MEASURING VAPOR TRANSMISSION THROUGH MATERIALS

BACKGROUND OF THE INVENTION

The present invention relates to a process for measuring the transmission of vapors through certain materials. The term "vapors" includes any of a wide variety of molecular particles suspended in the air through evaporative or other processes, such as water vapor. The term does not include natural gases such as oxygen, nitrogen, etc. More particularly, the present invention relates to a process for measuring vapor transmission rates through materials having a very high permeability; i.e., the material is relatively porous and, therefore, permits a fairly high volume of the vapor to pass through the material per unit of time.

The present systems for measuring vapor and gas transmission rates through materials are able to achieve highly accurate measurement results when the transmission rates through the materials are less than about 500 grams per square meter-day. In such systems, the resistance to the flow of vapor through the test setup is primarily governed by the material being tested, for the relatively slow vapor transmission rates observed are caused by the resistance to vapor flow afforded by the material, and only to a very much lesser extent by the flow resistance afforded by the air gaps within the test setup.

For purposes of the present invention, materials having a transmission rate in the range of 0–500 grams per square meter-day are considered to be low transmission rate materials. High transmission rate materials are defined as those materials which permit the passage of vapors at transmission rates in excess of 500 grams per square meter-day. For such materials, the overall observed vapor flow rate can be affected by the resistance to flow afforded by the air gaps in the test setup as well as by the material under test.

In any system for measuring vapor transmission rates, great care must be taken in controlling the important parameters which affect vapor transmission. In a typical test setup, the material to be tested is positioned to be a barrier to a source of vapor, and a vapor detector of one form or another is positioned on the downstream side of this barrier to measure the vapors which pass through the barrier. The driving force for creating the vapors is pressure and temperature; and these parameters must, therefore, be carefully controlled. In the typical test setup, the driving force is the vapor pressure of a liquid, determined at some atmospheric pressure and temperature, causing vapors from the liquid to diffuse through the enclosed chamber and ultimately through the material to be measured. If the transmission rate is very low, the vapor pressure can be presumed to be the same both at the surface of the liquid and at the surface of the material to be measured, and the vapor detector is typically at atmospheric pressure on the other side of the material. Therefore, the pressure drop across the test material is assumed to be simply the vapor pressure of the liquid creating the vapor, at the ambient temperature of the test setup. This assumption generally holds true for vapor transmission rates less than about 500 grams per square meter-day; but when the rate becomes larger than this number, the air gap in the enclosed chamber between the liquid and the test material becomes a factor that must be considered in the measurement. The pressure at the surface of the test material is not the same as the vapor pressure at the surface of the liquid, for an unknown pressure gradient will develop between the liquid surface and the material surface because of the higher vapor transmission rate. This unknown pressure gradient becomes more and more critical to the measurement process and, therefore, leads to highly inaccurate vapor measurement results, at transmission rates exceeding about 500 grams per square meter-day.

Because of the foregoing uncertainties encountered when attempting to measure vapor transmission rates through materials at high rates, it is extremely difficult to obtain accurate measurement data under these conditions. Among the techniques which have been tried in the past is the gravimetric technique, wherein liquid contained in a container which has been sealed by the material for which the transmission measurements are desired, is initially weighed on a very sensitive scale; and after a period of liquid evaporation, the same setup is weighed again. The weight loss is then calculated, and the transmission rate per unit of time is derived from this calculation. This technique will lead to the calculation of a value representative of vapor transmission rate through the material, but it leaves a high degree of uncertainty concerning the test conditions; i.e., pressure and temperature conditions across the material undergoing test.

It would, therefore, be an advantage to provide a process for measuring the rate of transmission of a vapor through a test material, wherein the measurement process can be very accurately determined and the measurement setup can be readily and conveniently constructed. The present invention accomplishes this purpose to great advantage and provides a significant advance in the arts.

SUMMARY OF THE INVENTION

The process for measuring the vapor transmission rate through a test material comprising the steps of enclosing a liquid source in a chamber having at least one wall wherein various material selections can be chosen; forming a further chamber on the outside of the material wall and having an inlet into the further chamber connected to an inert gas source and having an outlet from the further chamber connected to a vapor detector; selecting a first sample material of a known type for the chamber sealing wall and diffusing vapor through the chamber and first material and detecting and measuring the rate of transmission with the vapor detector; affixing a test material immediately adjacent the first material to form the chamber wall and again diffusing vapor through the combination of materials and the chamber to the vapor detector; calculating the transmission rate through the test sample by the equation $$1/T_{RT} = 1/T_{TOT} - 1/T_{RA}.$$

Where
 $T_{RT}$=Vapor transmission rate through the test sample.
 $T_{TOT}$=Total observed vapor transmission rate through both samples and the air gap.
 $T_{RA}$=Total observed vapor transmission rate through the known sample and the air gap.

This process assumes that the resistance to vapor flux afforded by the air gap is the same in both cases, and the two-step process enables the unknown resistance to vapor flux to be subtracted out of the two equations developed for vapor transmission rate calculation.

It is a principal object of the present invention to provide a process for measuring the vapor transmission rate of a particular and selected material.

It is a further object and advantage of the present invention to provide a process for measuring transmission rates through materials, according to a process that is easily and readily implemented.

It is a further object and advantage of the present invention to provide a process for measuring high vapor transmission rates to a high degree of accuracy.

The foregoing and other objects and advantages will become apparent from the following specification and claims and with reference to the appended drawings.

DESCRIPTION OF THE PREFERRED EMBODIMENT

Figure 1:
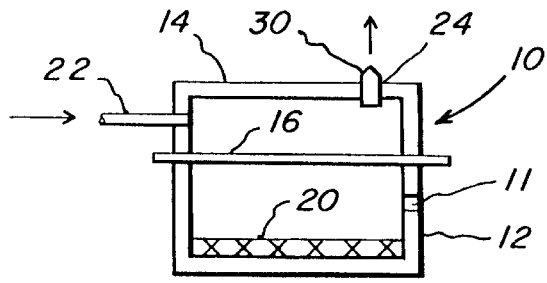
FIG. 1 shows a diagram of a test cell for measuring a single material sample.

FIG. 1 illustrates a typical test setup for conducting the process of measuring vapor transmission rates through materials. A test chamber 10 includes a lower compartment 12 and an upper compartment 14. Compartments 12 and 14 are respectively clamped together with a sample membrane 16 clamped between the compartments. A liquid source 20 is contained within the lower compartment, and vapors emanating from the liquid source 20 diffuse generally throughout the chamber formed between the membrane 16 and the lower compartment 12. A small vent opening 11 penetrates the wall of the lower compartment 12 in order to ensure that the overall pressure within compartment 12 is the same as the atmospheric pressure outside of the test device. The cross-section area size of this opening 11 is very small, perhaps 1/16th inch, especially as compared to the cross-sectional area of the membrane 16.

The upper compartment 14 has a gas inlet 22 and a gas outlet 24. A suitable vapor detector 30 is confined in or in association with the gas outlet 24. An inert carrier gas such as nitrogen is passed through the inlet 22 into the upper chamber created between the membrane 16 and the upper compartment 14, and out the exit passage 24. The carrier gas serves to collect any diffused vapors which may be in the upper chamber and to convey them to the vapor detector 30. The test setup illustrated in FIG. 1 is typically contained within a controlled temperature and pressure environment, and tests which are conducted in sequence are conducted under constant temperature and pressure conditions.

Figure 2:
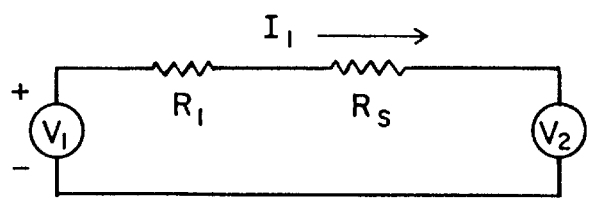
FIG. 2 shows the electrical circuit dual of the apparatus of FIG. 1.

FIG. 2 shows an electrical dual of the physical test setup of FIG. 1 and serves to illustrate the process of the present invention in electrical terminology. The voltage source $V_1$ is the electrical analog of the vapor pressure driving force at the surface of the liquid source 20. The liquid vapor pressure at the ambient pressure and temperature of the test setup is a known or derivable quantity. The voltage source $V_2$ is the electrical analog of the vapor pressure measured at the vapor detector 30. The resistance $R_1$ is the electrical analog of the resistance to diffusion caused by the air gaps contained within the test chamber 10, which resistance leads to an unknown pressure gradient across the test zone. The resistance $R_s$ is the electrical analog of the sample membrane 16, through which the vapors diffuse. The current value $I_1$, is the electrical analog of the vapor flux which flows through the test chamber at a constant rate, conveying the vapor to the vapor detector 30. In electrical terms the values "R" are equal to the reciprocal of the admittance of the respective physical quantities, which in terms of the test setup is equivalent to the reciprocal of the transmission rate. Therefore, the value $R_1$ is the reciprocal of the transmission rate across the air gap in the test setup; the value $R_s$, is the reciprocal of the transmission rate through the membrane 16. The values $R_1$ plus $R_s$, equal the reciprocal of the total transmission rate, including the air gaps and the membrane 16.

The value $V_1$ is equal to the vapor pressure at the surface of the liquid source 20, and is assumed to be at 100% relative humidity, taken at the test temperature and pressure. If we assume the liquid to be water, the value $V_1$ is the vapor pressure of water at the ambient pressure and temperature of the test setup. In this case, the value $V_2$ is equal to the vapor pressure of the liquid ($V_1$) multiplied by the relative humidity of the carrier stream, taken at the test temperature and pressure. The current value $I_1$, is the electrical analog of the volume flow rate per unit time of the vapor, at the test temperature and pressure. The value $V_1$ is a known quantity if the test temperature and pressure are known and the liquid in the liquid source is known. The value $V_2$ is a known quantity since it can be calculated by measuring the relative humidity at the exit 24 and multiplying this value times the value $V_1$.

The values $R_1$ and $R_s$ are both unknown, for the pressure gradient across the air gap is initially an unknown value. The physical equivalent for the value of $I_1$ can be measured by the vapor detector apparatus which is placed in the path of the exit gas through the upper chamber. For example, in a test setup which utilizes water as the test liquid, the vapor detector 30 can be an instrument for measuring relative humidity. The carrier gas will typically be nitrogen, and the flow rate of the carrier gas will be carefully controlled and known. Therefore, the physical value equivalent to the current value $I_1$ can be calculated by taking the carrier gas flow rate measured in volume flow per unit time, and multiplying it times the relative humidity measured by the vapor detector 30, times a variable K(T,P). The variable K(T,P) is determined at 100% relative humidity of water, and is the weight of vapor per cubic centimeter,(cc) under the test conditions of temperature and pressure. The variable K(T,P) can be determined from a handbook of chemistry and physics, or it can be calculated.

The foregoing known and measured quantities will lead to the calculation of the total vapor transmission rate ($T_{RA}$) in the test setup of FIG. 1:

$$(R_1 + R_s) = \frac{(V_1 - V_2)}{I_1} = \frac{1}{(T_{RA})}$$

$$(T_{RA}) = \frac{I_1}{(V_1 - V_2)}$$

It should be noted that the foregoing analysis does not yield the vapor transmission rate of the membrane 16 per se, but merely yields the vapor transmission rate through the entire test cell, including the chamber air gaps and the membrane 16. This limitation occurs because it is impossible to measure the vapor pressure of the surface of the membrane 16, due to the unknown pressure gradient which occurs across the air gap. Of course, the membrane 16 is presumed to be a high transmission rate membrane of a known type, for which there is no particular interest in determining the specific vapor transmission rate.

Figure 3:
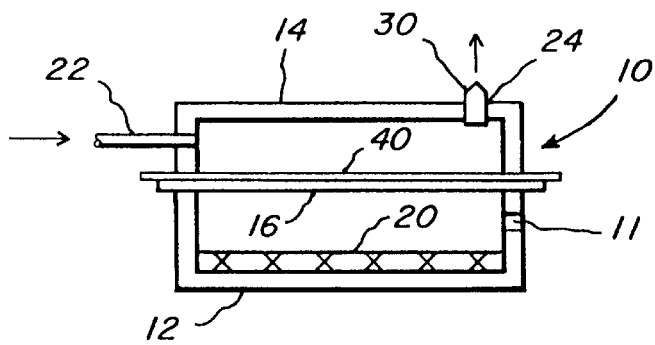
FIG. 3 shows a diagram of a test cell for measuring diffusion rates through the combination of a material sample and a test sample.
Figure 4:
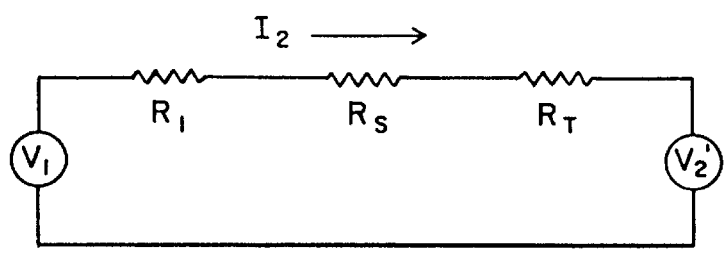
FIG. 4 shows an electrical circuit dual of the apparatus of FIG. 3.

The illustrations of FIGS. 3 and 4 show the further steps of the process necessary for calculating the vapor transmission through a test membrane for which such information is desired. FIG. 3 illustrates the same test cell 10 and the same liquid reservoir 20, with carrier gas input 22 and an exit passage 24, and a vapor detector 30. In the example of FIG. 3, the test cell setup is identical to that illustrated in FIG. 1 with the exception that a test membrane 40 is overlaid over the sample membrane 16, and both membranes are clamped between the upper and lower housings 14 and 12. The same conditions are applied to the test setup of FIG. 3 as have been discussed relative to the test setup of FIG. 1. After evaporation conditions have stabilized, the vapor detector 30 is used to measure the vapor escaping from exit 24. In the case of a test conducted with water as the liquid contained in reservoir 20, the vapor detector 30 is a relative humidity sensor.

FIG. 4 illustrates the electrical dual of the physical setup of FIG. 3, and is similar to the diagram of FIG. 2 with the exception that an additional resistance $R_T$ is inserted into the circuit. The value $V_1$ continues to represent the vapor pressure driving force at the surface of the liquid reservoir 20, and the voltage $V_2'$ represents the vapor pressure driving force at the exit 24. The value of $V_2'$ is calculated by multiplying the value $V_1$ by the measured relative humidity detected by vapor detector 30. This measured relative humidity may very well be different from the relative humidity measured during the analysis steps associated with FIGS. 1 and 2. Similarly, the current $I_2$ is calculated by multiplying the carrier gas flow rate by the measured relative humidity percentage and the variable K(T,P), it being presumed that the test conditions relating to temperature and pressure are identical to the test conditions of the analysis conducted with respect to FIGS. 1 and 2. The foregoing known and measured quantities will lead to the calculation of the vapor transmission rate ($T_{TOT}$) of the test setup of FIG. 3:

$$R_1 + R_S + R_T = \frac{V_1 - V_2'}{I_2} = \frac{1}{T_{TOT}}$$

$$T_{TOT} = \frac{I_2}{V_1 - V_2'}$$

Since the value of the sum ($R_1+R_s$) is known from the previous calculation, the value $R_T$ can be determined.

$$R_T = \frac{1}{T_{RT}} = \frac{V_1 - V_2'}{I_2} - \frac{V_1 - V_2}{I_1}$$

$$T_{RT} = \frac{1}{\frac{(V_1 - V_2')}{I_2} - \frac{(V_1 - V_2)}{I_1}}$$

The value of $T_{RT}$ is the vapor transmission rate through the test membrane 40, which is usually stated in terms of grams per unit time per millimeter of mercury pressure.

Figure 5:
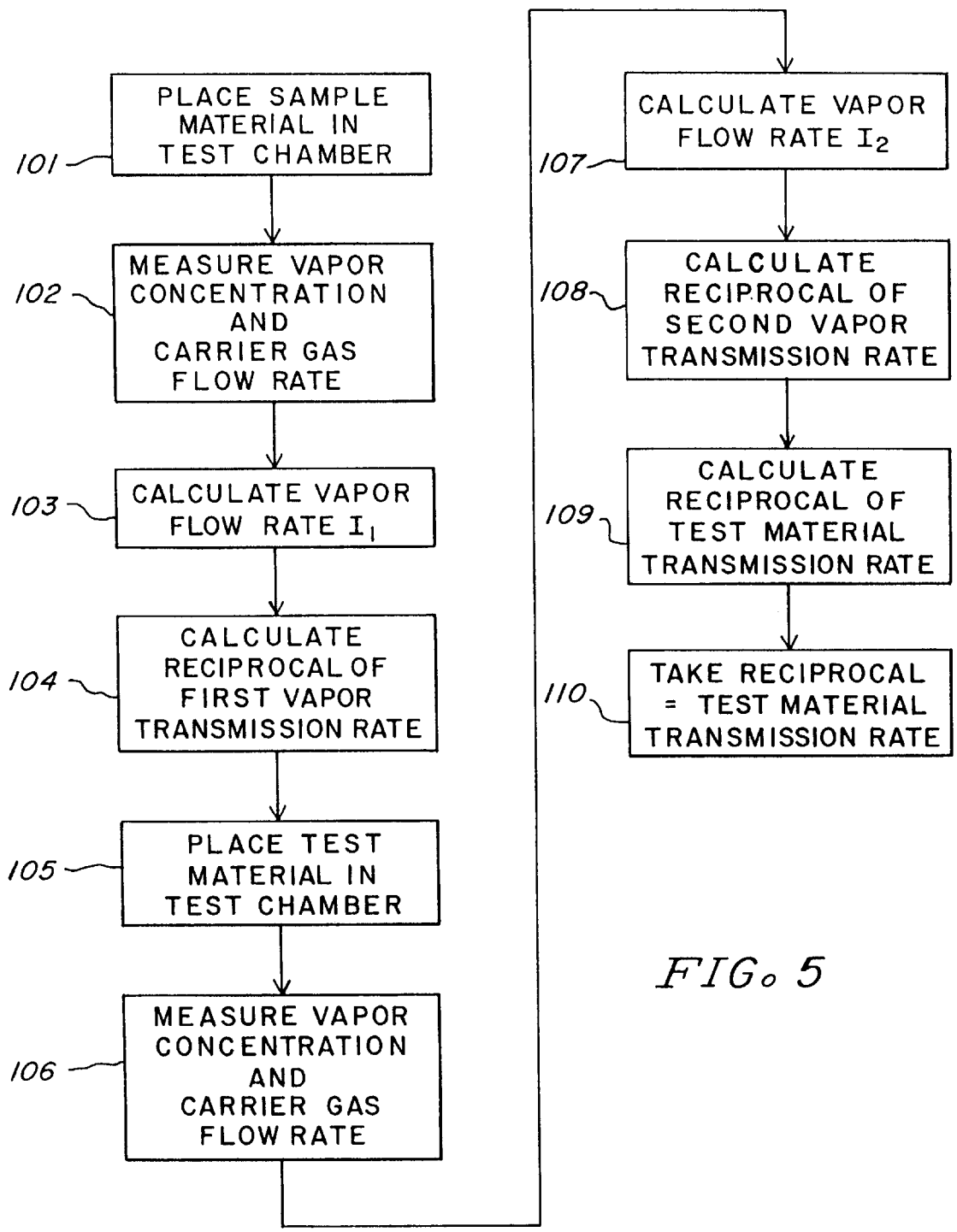
FIG. 5 shows a process diagram.

FIG. 5 shows a flow diagram of the process described above. At step 101, the known sample material is placed into the test chamber and is subjected to the evaporative process of whatever liquid is confined in the lower test chamber; and a carrier gas is supplied through the upper chamber. It is presumed that the ambient temperature and pressure conditions are kept constant, and the carrier gas flow rate is carefully measured; the evaporative process continues until stabilized conditions have been reached.

At step 102, a reading of the vapor detector is taken and the carrier gas flow rate is monitored. At step 103, the carrier gas flow rate is multiplied by the vapor detector reading and the variable K(T,P) to provide a first vapor flow rate in terms of weight of vapor per unit time passing through the test cell outlet.

At step 104, a calculation is made to determine the reciprocal of the first vapor transmission rate; this value is determined by subtracting the product of the vapor pressure driving force and the measured relative humidity from the vapor pressure driving force and dividing the result by the calculated vapor flow rate $I_1$.

At step 105, the test chamber is opened and a test material is placed into the test chamber immediately adjacent the sample material which was previously placed in the test chamber. Again, the apparatus is monitored until stabilized conditions have occurred.

At step 106, the vapor detector measurement is taken and the carrier gas flow rate is carefully monitored. At step 107, a new calculation of the vapor flow rate ($I_2$) is made using the test conditions resulting from the new test setup. At step 108, the reciprocal of the second vapor transmission rate is calculated in the same manner as described earlier with respect to the first transmission rate.

At step 109, the reciprocal of the test transmission rate as calculated by subtracting the reciprocal of the second vapor transmission rate from the reciprocal of the first vapor transmission rate. Finally, at step 110 the reciprocal value of the result obtained in step 109 is taken to reveal the test material transmission rate.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. A process for measuring the vapor transmission rate through a test material under controlled ambient pressure and temperature conditions, comprising the steps of:

a) forming a two-chamber device having a sample material as a barrier wall between the two chambers, and a liquid vapor-producing source having a liquid surface and a known vapor pressure in one chamber and a carrier gas inlet and outlet in the second chamber with a vapor detector positioned to detect vapors passing through the outlet;

b) measuring the carrier gas flow rate and the percentage vapor detected by the vapor detector;

c) calculating the vapor flow rate at said outlet;

d) calculating the vapor pressure drop between the liquid surface and said outlet;

e) calculating a first total vapor transmission rate ($T_{RA}$) through said device by dividing the vapor flow rate by the vapor pressure drop between the liquid surface and said outlet;

f) applying a test material adjacent the sample material in said two-chamber device;

g) repeating steps b) through d);

h) calculating a second total vapor transmission rate ($T_{TOT}$) through said device by dividing the second calculated vapor flow rate by the second calculated vapor pressure drop; and i) calculating the vapor transmission rate ($T_{RT}$) through said test material by the equation:

$$1/T_{RT} = 1/T_{TOT} - 1/T_{RA}.$$

2. The process of claim 1, wherein the step of calculating the vapor flow rate passing through said outlet further comprises multiplying said measured carrier gas flow rate by said percentage vapor detected by said vapor detector.

3. The process of claim 1, wherein the step of calculating said vapor pressure drop between said liquid surface and said outlet further comprises multiplying said known vapor pressure by said percentage vapor detected by said vapor detector.

4. The process of claim 1, wherein said liquid further comprises water, and said vapor detector further comprises means for detecting relative humidity, and the steps of calculating said first and second vapor transmission rates each include measuring the percentage relative humidity of said carrier gas.

5. A process for measuring the water vapor transmission rate through a test material under controlled pressure and temperature conditions in a test cell having an upper and lower chamber separated by a sample barrier material, and a water source having a known saturated vapor pressure in said lower chamber, and a carrier gas inlet into said upper chamber and a gas outlet from said upper chamber, and a device for measuring relative humidity in gases flowing through said gas outlet, comprising the steps of:

a) flowing carrier gas into said gas inlet at a known volume flow rate;

b) measuring the percentage relative humidity of said carrier gas;

c) calculating a first value flow rate which is the product of the relative humidity, the carrier gas flow rate and a variable K(T,P) which is the weight of vapor per cubic centimeter under the test conditions of temperature and pressure;

d) reducing the value of the known saturated water vapor pressure by a value which is the product of the known saturated water vapor pressure and the percentage relative humidity, to yield a first reduced water vapor pressure value;

e) calculating the reciprocal of a first water vapor transmission rate by dividing the first reduced water vapor pressure value by the first value flow rate;

f) placing a test material adjacent said sample barrier material between said upper and lower chambers;

g) measuring a new percentage relative humidity in said carrier gas;

h) calculating a second value flow rate which is the product of the new percentage relative humidity, the known carrier gas flow rate and a value K(T,P) which is the weight of vapor per cubic centimeter under the test conditions of temperature and pressure;

i) reducing the known saturated water vapor pressure by a second value which is the product of the known saturated water vapor pressure and the measured relative humidity to yield a second reduced water vapor pressure value;

j) calculating the reciprocal of a second water vapor transmission rate by dividing the second reduced water vapor pressure value by the second value flow rate; and k) subtracting the reciprocal of the first water vapor transmission rate from the reciprocal of the second water vapor transmission rate and taking the reciprocal of the result to determine the water vapor transmission rate through the sample barrier material.

6. A process for measuring the vapor transmission through a test material, by using a two-chamber test cell wherein a membrane forms a barrier between the two chambers, and the lower chamber contains a liquid source having a known vapor pressure and the upper chamber has a constant flow value of an inert carrier gas through the upper chamber and into a vapor detector; comprising the steps of:

a) measuring the percentage vapor in said carrier gas flow with said vapor detector;

b) reducing the known vapor pressure by a value which is the product of the known vapor pressure and the measured percentage vapor in the carrier gas flow;

c) reducing the constant flow value of said inert carrier gas by multiplying it by the measured percentage vapor;

d) dividing the reduced known vapor pressure by the reduced constant flow value to form a vapor transmission value;

e) affixing the test material adjacent said membrane as a further barrier between said two chambers;

f) repeating steps a) through d) to form a further vapor transmission value; and g) subtracting said further vapor transmission value from said first-calculated vapor transmission value, to produce a value which is the vapor transmission rate through said test material.

7. The process of claim 6, wherein liquid source further comprises water and the step of measuring the percentage vapor in said carrier gas further comprises measuring the percent relative humidity of said carrier gas.

\* \* \* \* \*